US00PP28248P3

(12) United States Plant Patent
Warren

(10) Patent No.: US PP28,248 P3
(45) Date of Patent: Aug. 8, 2017

(54) CHERRY TREE NAMED 'JFS-KW14'

(50) Latin Name: *Prunus*
Varietal Denomination: JFS-KW14

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 99 days.

(21) Appl. No.: 14/757,326

(22) Filed: Dec. 16, 2015

(65) Prior Publication Data

US 2017/0181345 P1 Jun. 22, 2017

(51) Int. Cl.
*A01H 5/02* (2006.01)

(52) U.S. Cl.
USPC ..... Plt./182

(58) Field of Classification Search
USPC ..... Plt./182
See application file for complete search history.

(56) References Cited

PUBLICATIONS

"First Blush Cherry", Nursery Management, Dec. 4, 2015, www.nurserymag.com/product/first-blush-cherry, p. 1.*

* cited by examiner

*Primary Examiner* — Anne Grunberg
(74) *Attorney, Agent, or Firm* — Klarquist Sparkman, LLP

(57) ABSTRACT

A variety of ornamental cherry that combines a strongly upright branch habit, a narrow form, bright pink double flowers, and an early flowering date.

11 Drawing Sheets

Latin name of the genus and species of the plant claimed and variety denomination: *Prunus* 'JFS-KW14'.

BACKGROUND OF THE INVENTION

As a part of an ornamental cherry selection program, in 2001, I picked seed from an unnamed unpatented hybrid seedling of 'Okame' (*Prunus×incam* 'Okame') that had double flowers but was otherwise unremarkable. I raised several hundred seedlings from these seeds in seedbeds in a nursery in Boring, Oreg. From these, I selected the strongest 108 seedlings and planted them in a row in the same nursery in May, 2003. I evaluated the growth and appearance of these seedlings several times each season in 2003 through 2005. In the fall of 2005, I selected the 11 best seedlings to keep and I discarded the rest. I transplanted these 11 selected seedling trees to another row in the same nursery in January 2006 for further evaluation. By the fall of 2007, I had chosen two of these trees as having the best potential for introduction as a cultivar. I discarded the other nine trees and planted the two best trees into a long term evaluation block in the same Boring, Oreg. nursery. I named one of these trees 'JFS-KW14'. I was first attracted to this particular tree because of its uniquely narrow upright shape and its bright pink double flowers.

In each year from 2007 through 2012, I asexually test propagated 'JFS-KW14' by chip budding onto *Prunus avium* rootstock in small experimental plots in a Canby, Oreg. nursery, propagating a total of 143 trees during these years. All of these trees were subsequently destroyed after field testing except for those kept to provide for stock increase: 16 planted in a Boring, Oreg. nursery and 25 planted in the Canby, Oreg. nursery. I also propagated trees of my new variety by rooting summer softwood cuttings during 2011 through 2014. A total of 1547 cuttings were successfully propagated in this manner and were planted under my direction in the Canby, Oreg. nursery, where they are still growing in the location they were planted. From all of this propagation, I determined that the characteristics of my new variety and firmly fixed and all propagated plants have been identical to my new variety in every way observed.

SUMMARY OF THE INVENTION

This new cultivar possesses a unique combination of characteristics in that it combines a strongly upright branch habit, a narrow form, bright pink double flowers, and an early flowering date.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
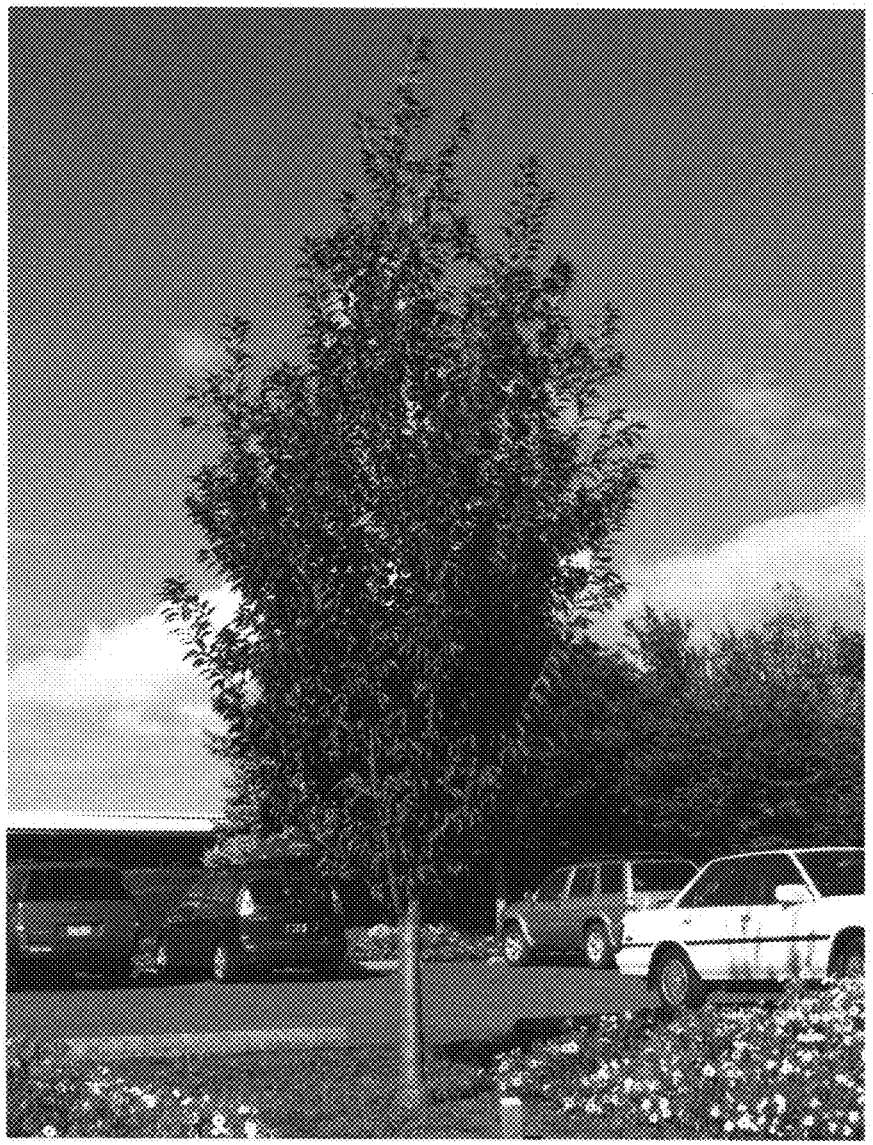
FIG. 1: Shows the upright branch habit and form of a 13 year old tree with summer foliage.
Figure 2:
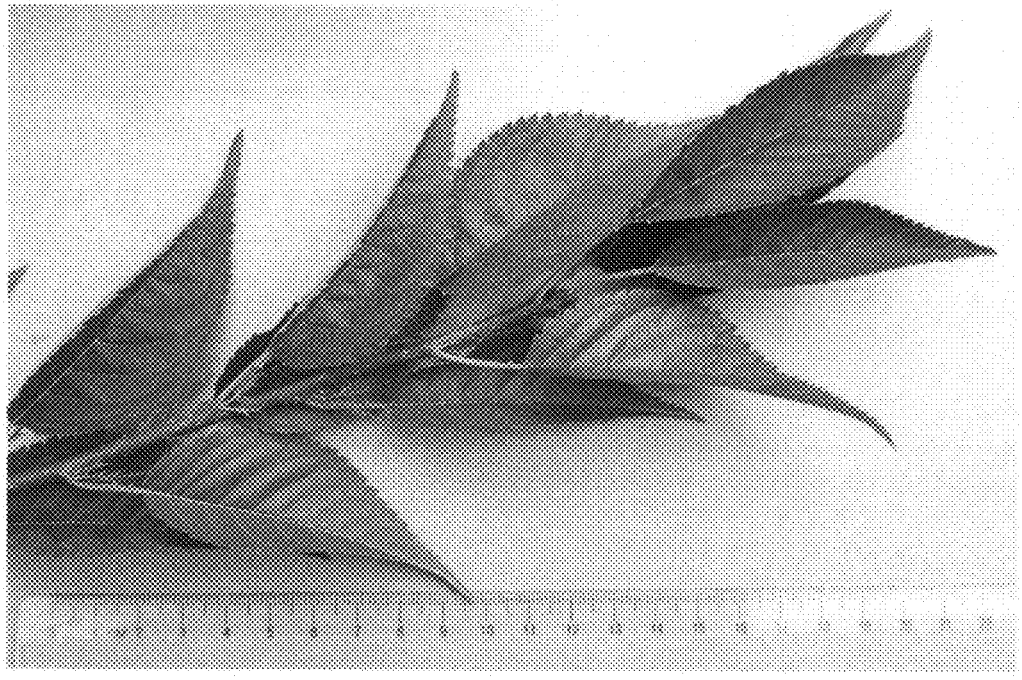
FIG. 2: Shows the Summer foliage color on a display board with a scale.
Figure 3:
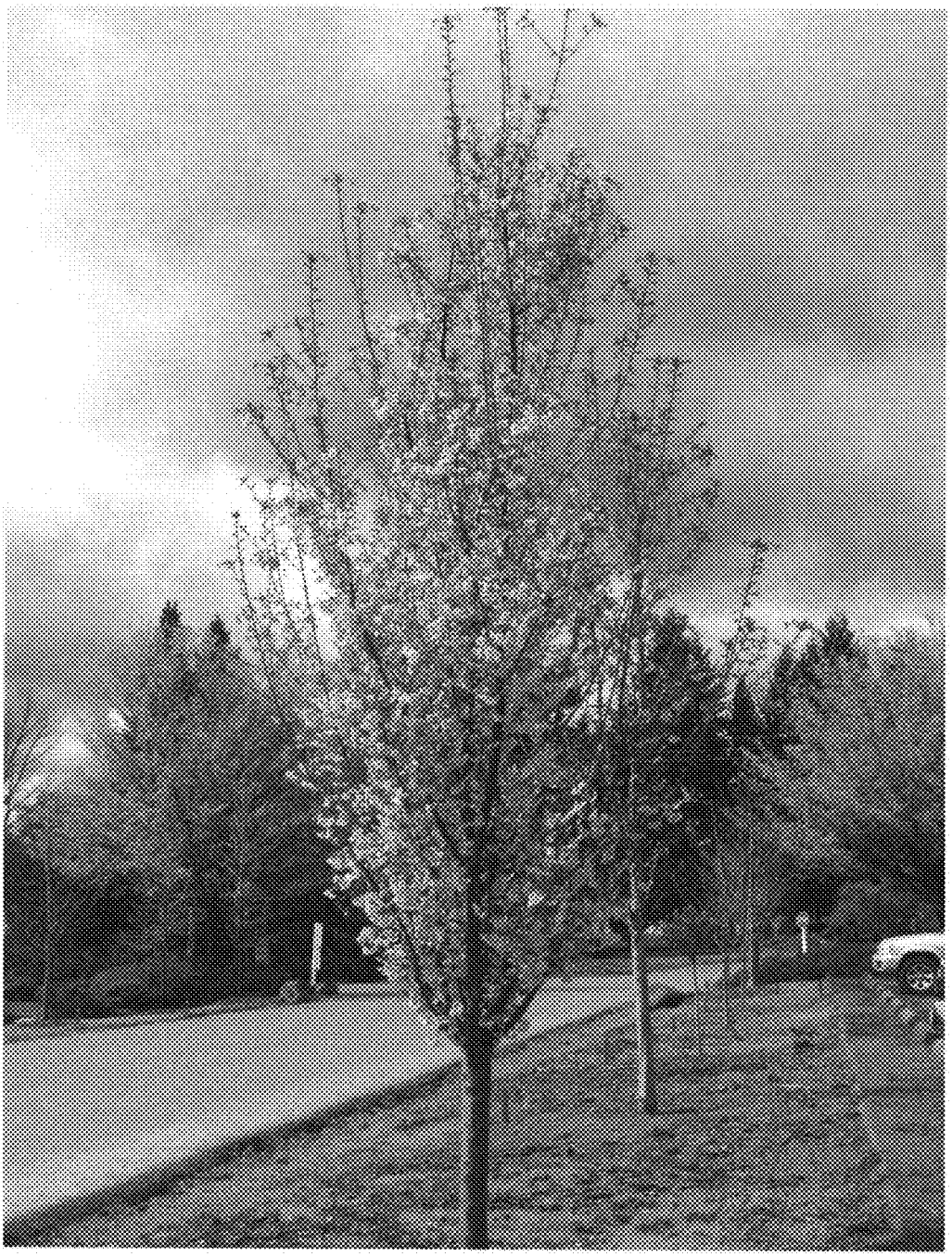
FIG. 3: Shows the upright branch habit & form as well as the prolific flowering of a 13 year old tree.
Figure 4:
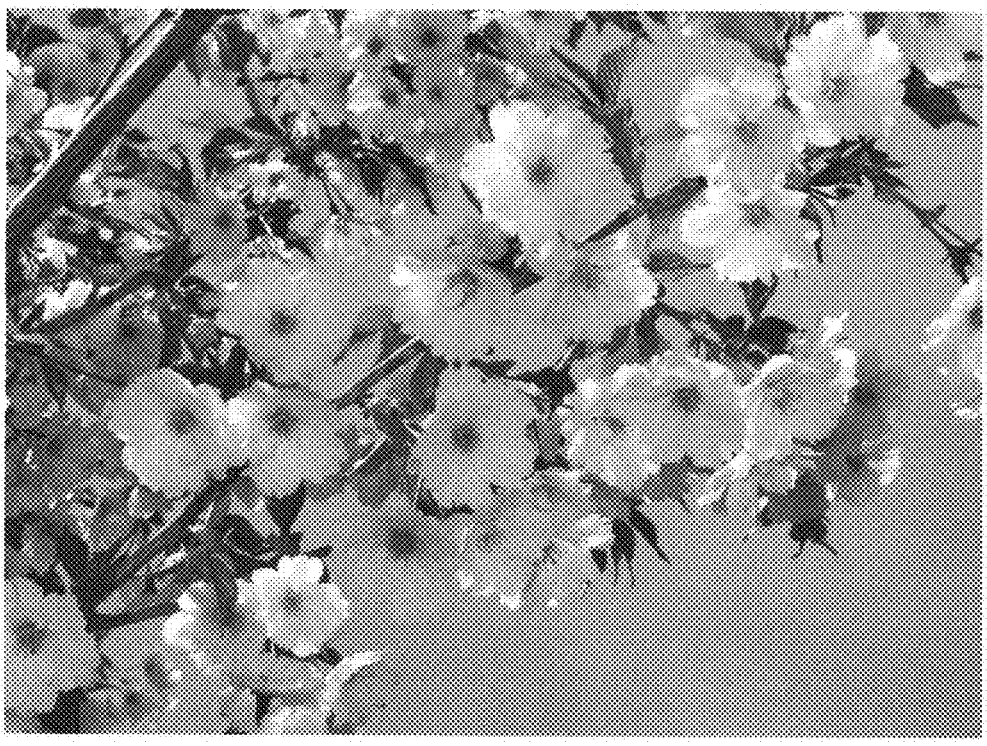
FIG. 4: Shows a close up the flowers on some branches of a 13 year old tree.
Figure 5:
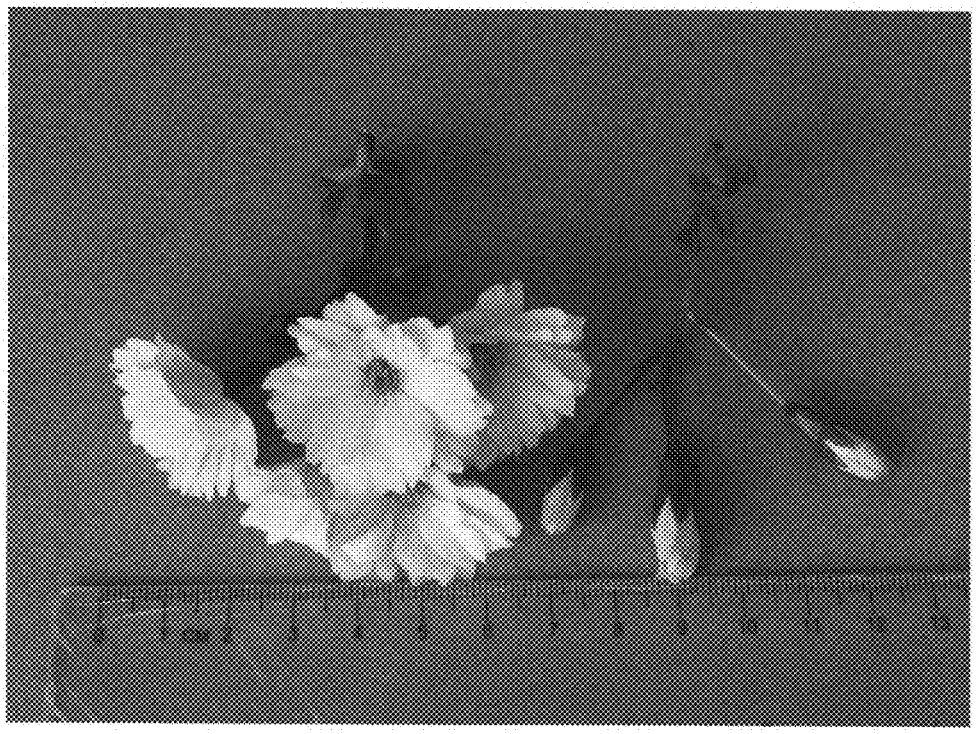
FIG. 5: Shows a close-up of 2 corymbs of flowers, one open and one in bud on a display board with a scale.
Figure 6:
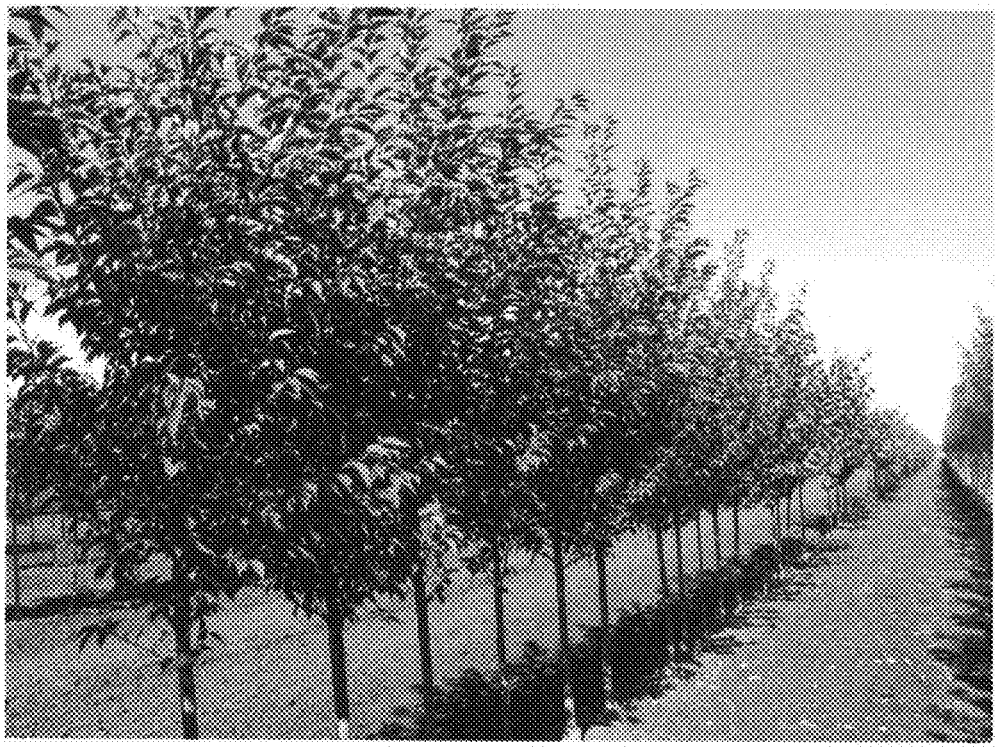
FIG. 6: Shows 2 year old vegetatively propagated trees growing in a nursery row.
Figure 7:
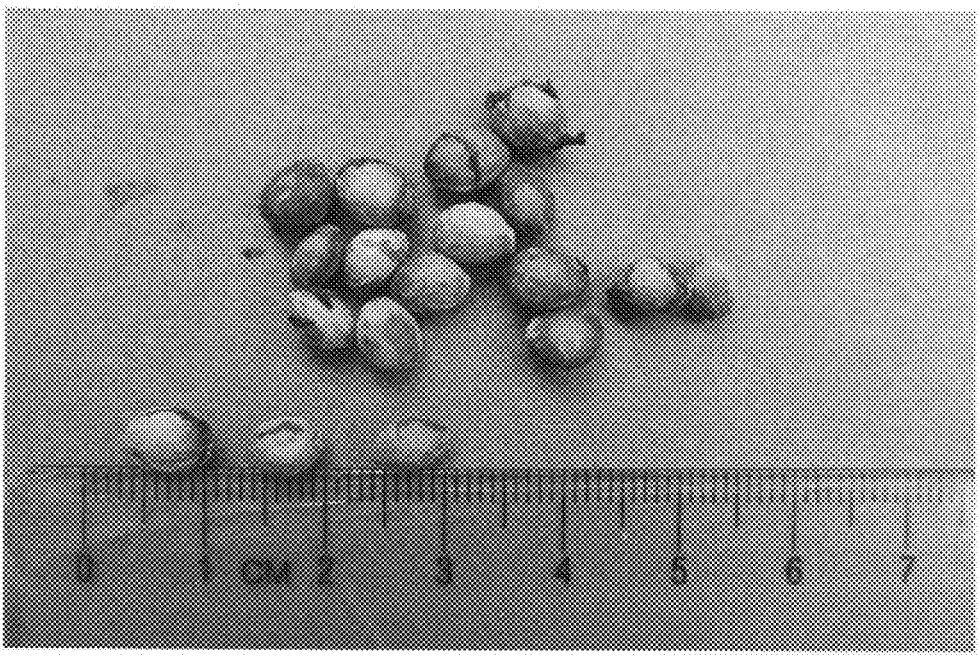
FIG. 7: Shows the seed to be a slightly flattened ovoid stone.
Figure 8:
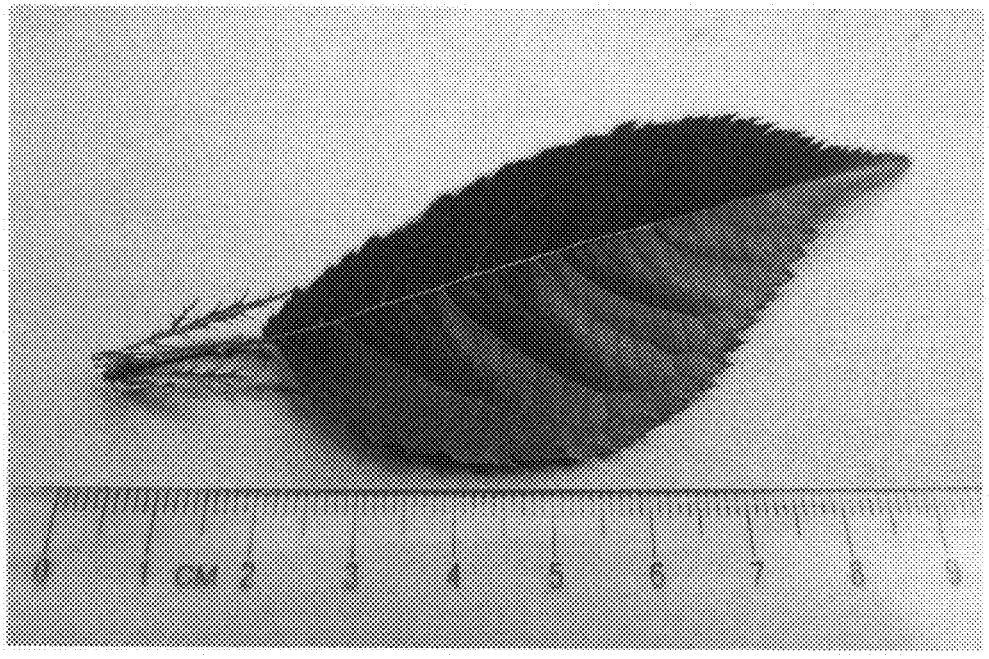
FIG. 8: Shows a single summer leaf and stipules on a display board with a scale.
Figure 9:
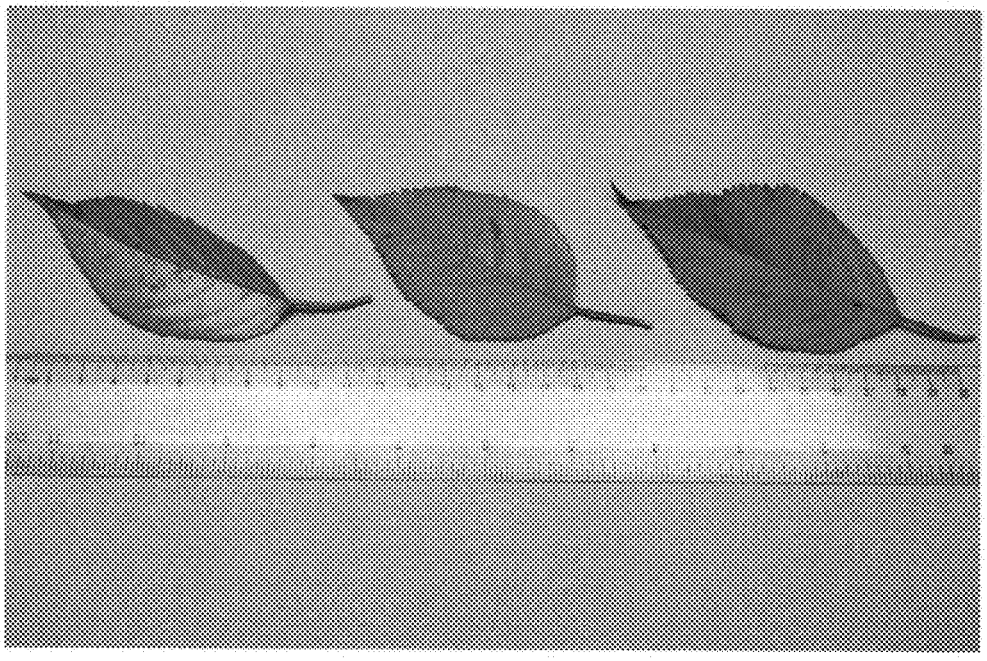
FIG. 9: Shows the Yellow Orange to Orange Red fall color of the foliage on a display board with a scale.
Figure 10:
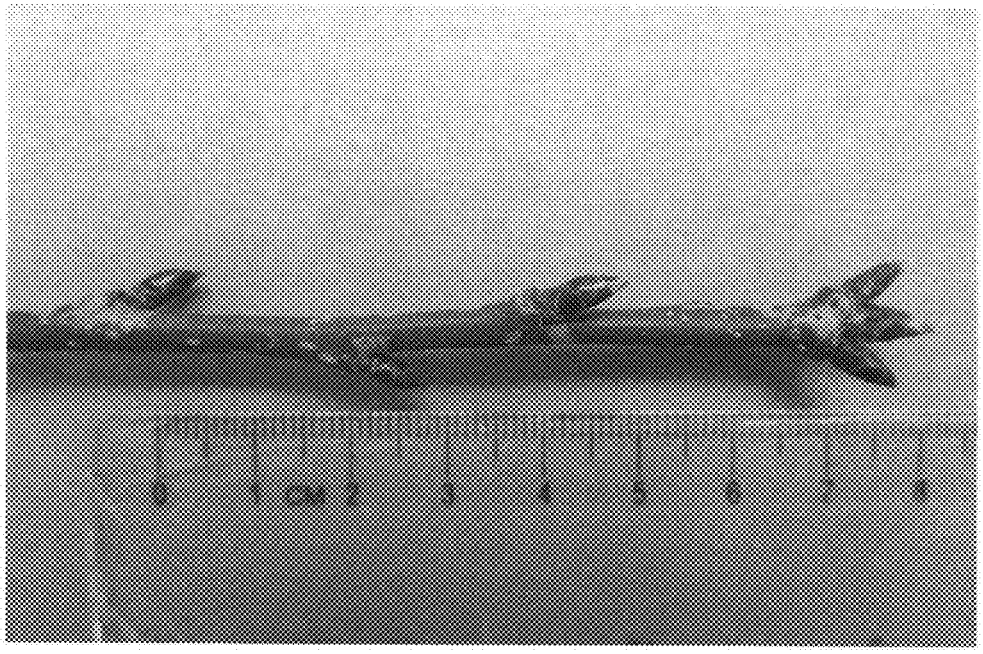
FIG. 10: Shows a winter twig with bud arrangement on a display board with a scale.
Figure 11:
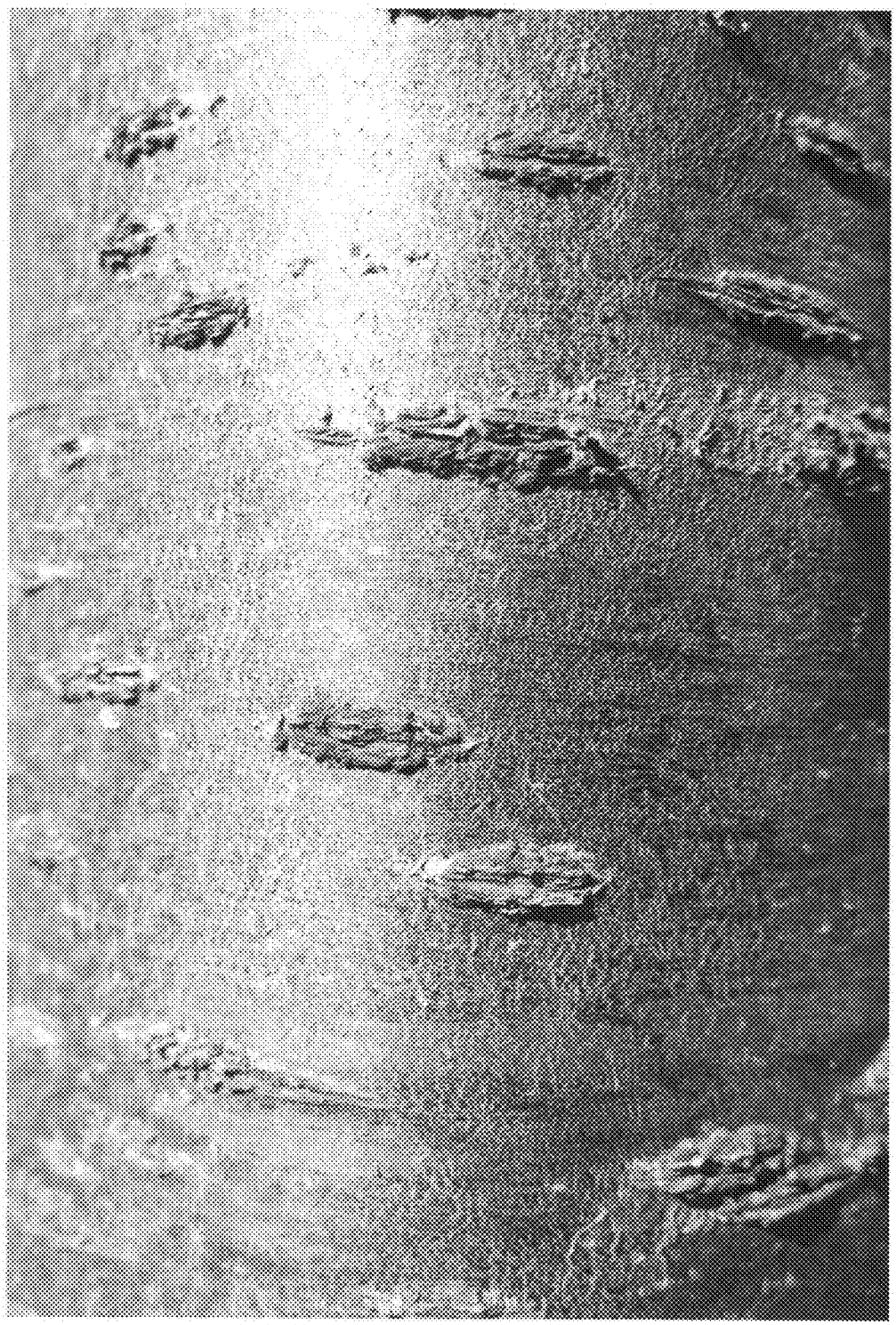
FIG. 11: Shows mature bark and large horizontal lenticels on a 13 year old tree

The following detailed description of the 'JFS-KW14' variety is based on observations of the original tree growing in Boring Oreg. and one, and two year old progeny. The observed progeny were trees which were growing in Canby, Oreg.

The following is a detailed description of my new cherry tree with color descriptions using terminology in accordance with The Royal Horticultural Society (London) Colour Chart© 1986, except where ordinary dictionary significance of color is indicated.

Scientific name: *Prunus* 'JFS-KW14'.

Parentage:

*Seed parent.*—A hybrid seedling of *Prunus×incam* 'Okame' (unpatented).

*Pollen parent.*—Unknown.

Tree:

*Overall shape.*—Strongly upright branch orientation forming a narrow inverted cone, widest near the top, primary branches are angled at 20 degrees to 30 degrees from the vertical.

*Height.*—6.4 meters at 13 years of age.

*Width.*—2.3 meters at 13 years of age.

*Caliper.*—14.7 cm at 10 cm height above ground and 9.9 cm at 1 meter above ground at 13 years of age.

*Trunk.*—Stout, straight.

*Trunk bark texture.*—Smooth with prominent lenticels, becoming vertically fissured with age.

*Trunk bark color.*—Immature bark color: Greyed Orange 172A to 172C. Mature bark color: Brown 200A to Greyed Green 197A showing a mix of both colors. Lenticels: Oval to long oval 5 mm to 30 mm long and 2 mm to 5 mm wide. Horizontal orientation. Greyed Orange 166C.

*Primary branches.*—Stiffly upwards spreading at 20° to 30° from the vertical.

*Branch color.*—Greyed Orange 166A.

*Branch lenticels.*—Oval to long oval, Greyed Orange 164D. 1 mm to 3 mm long by 1 mm wide.

*Dormant buds.*—Narrow, conical with acute tip and with imbricate scales. 4 mm to 7 mm long by 2 mm to 3 mm in diameter. Greyed Orange 177A to Greyed Purple 183B.

*Internodes.*—Average 23 mm on 2 year trees with a range of 15 mm to 30 mm.

*Hardiness.*—Has tolerated field temperatures to 9 degrees F. without damage in Canby, Oreg. This is the minimum temperature this location experienced during the life of the tree. It is believed to have Zone 5 cold hardiness similar to other plants of this species.

*Disease resistance.*—It has shown moderately good resistance brown rot and shot hole disease.

Leaves: Except as otherwise noted, observations are from twenty vigorous growth leaves.

*Arrangement.*—Alternate.

*Type.*—Simple.

*Texture.*—Smooth.

*Sheen.*—Satin.

*Length.*—7.5 cm to 9 cm, averaging 8.3 cm on leaves from 2 year old nursery trees.

*Width.*—4.5 cm to 5 cm, averaging 4.6 cm on leaves from 2 year old nursery trees.

*Petioles.*—1.5 cm to 2.2 cm long, averaging 1.8 cm on leaves from 2 year old nursery trees. Diameter 1.3 mm.

*Overall shape.*—Simple, ovate to oval.

*Margin.*—Serrate to doubly serrate.

*Tip.*—Acuminate to long acuminate.

*Base.*—Acute to broadly acute.

*Stipules.*—Prominent, 20 mm to 25 mm long, 2 mm to 4 mm wide, lanceolate with dissected branching and glandular branch tips.

*Spring leaf color.*—First emerging leaves Yellow Green 148A.

*Summer leaf color.*—Upper leaf surface: Green 137A to Green 139A. Lower leaf surface: Green 137C to Green 138B. Bud break averages March 10th in Canby, Oreg. depending on spring weather conditions.

*Fall leaf color.*—Leaves along the branches first turn Yellow Orange 21B to Orange Red 30. Color can be more intense on the branch tips ranging from Orange Red 34 to Red 42.

*Timing of fall leaf color.*—Average dates for original tree in Boring, Oreg. Onset: Nov. 10, 2015. Peak: Nov. 22, 2014, Nov. 17, 2015. Latest extent of fall color: Nov. 28, 2014, Nov. 23, 2015. Fall color begins and peaks at a time that is typical for the species.

*Defoliation.*—Complete defoliation averages November 30 in Boring, Oreg.

*Pubescence.*—None.

*Persistence.*—The tree is deciduous.

Flowers:

*Overall.*—Perfect, fully double, typically with 15 petals in 3 series of 5. Flowers held in corymbs of 3 to 6, typically 5.

*Size.*—Round and symmetrical. On first opening somewhat bell shaped 15 mm deep by 20 mm in diameter, opening to 28 mm to 35 mm in diameter, then flattening to 10 mm deep.

*Flower buds.*—Similar to vegetative buds but broader, 4 mm to 8 mm by 3 mm to 4 mm in diameter.

*Color.*—Unopened buds: Red Purple 63B as the buds swell. Opened flowers: Red 49D to Red Purple 65C.

*Petals.*—Red 49D to Red Purple 65C, usually opening to Red 49D and then becoming Red Purple 65C as the flowers age. 12 mm to 16 mm long by 7 mm to 10 mm wide. Broadly obovate, notched at the tip.

*Sepals.*—Five, acute 7 mm long and 3 mm wide, reflexed, connate at the base forming a tubular hypanthium 10 mm long by 3 mm in diameter.

*Stamen.*—Many, typically 40 to 50, 5 mm to 7 mm long, centrally clustered surrounding the pistil.

*Anthers.*—Small ovoid, approximately 0.5 mm by 0.3 mm, Yellow Orange 15B.

*Pistil.*—Single, usually one per flower but occasionally 2 if 2 ovules are present. 10 mm to 12 mm long by 0.5 mm in diameter. Undivided with single capitate style. Red 39B.

*Ovary.*—Superior contained within the base of the hypanthium, ovoid 2 mm high by 1.5 mm in diameter. Green 143C, usually 1 per flower but occasionally 2.

*Pollen.*—Yellow Orange 15B.

*Pedicel.*—5 cm to 8 cm in length by 1 mm to 2 mm in diameter. Yellow Green 146C. Pedicel branches 3 to 6 times with serrulate, lanceolate bracts at the base of each branch. Bracts 6 mm to 15 mm long by 4 mm to 9 mm in diameter. Green 139B.

*Pubescence.*—None.

*Fragrance.*—Very slight almost imperceptible, sweet.

*Flowering date in Boring Oreg.* 2015.—First boom: Mar. 10, 2015. Peak bloom: Mar. 17, 2015. End bloom: Mar. 25, 2015. Cherry bloom was about 2 weeks earlier than average in 2015. Fruit maturity occurs from early to mid-June in Oregon depending on the environmental conditions.

Fruit: Observations are from a sampling of typical fruit.

*Description.*—A drupe, one seeded. 7 mm to 10 mm long by 5 mm to 8 mm in diameter. Ovoid, glossy, smooth.

*Color.*—Red 46A, as it ripens becoming Greyed Purple 187A.

*Seed.*—A slightly flattened ovoid stone, 5 mm to 7 mm long by 5 mm to 6 mm in diameter. Greyed Orange 164D.

*Fruit production.*—Moderate.

*Usage.*—Wildlife value, taken quickly by birds.

COMPARISON TO OTHER CULTIVATED VARIETIES

Table 1 defines these differences when compared to the most similar commercial cultivars of ornamental cherry.

TABLE 1

| Feature: | 'JFS-KW14' | *Prunus serrulata* 'Kwanzan' (unpatented) | *Prunus* 'Okame' (unpatented) |
|---|---|---|---|
| Leaf length | 83 mm | 115 mm | 75 mm |
| Leaf width | 46 mm | 60 mm | 37 mm |
| Petioles | 18 mm | 25 mm | 14 mm |
| Branches Angles | 20 to 30 degrees | 40 to 55 degrees | 50 to 60 degrees |
| Flowers | Double | Very double | Single |
| Flower Diameter | 28 mm to 35 mm | 50 mm average | 20 mm to 25 mm |
| Petal count | 15 average | 25 to 50 | 5 |
| Petal series | 3 usually | 5 or more | 1 |
| Flowering Date | Early | Later | Very early |
| Peak Bloom | Mar. 17$^{th}$, 2015 | Apr. 1$^{st}$, 2015 | Mar. 10$^{th}$, 2015 |

COMPARISON TO THE SEED PARENT

Compared to the seed parent tree which was an unnamed hybrid seedling of 'Okame', my new variety 'JFS-KW14' has a more upright shape, more fully double flowers, and a brighter more intensely colored flower. The unnamed parent hybrid seedling had a more spreading oval shape, moderately double flowers with usually 10 petals, and a flower color slightly lighter than Red 49D. My new variety 'JFS-KW14' is strongly upright forming a narrow inverted cone shape, has fully double flowers usually with 15 petals, and a brighter flower color Red 49D to Red Purple 65C.

I claim:

1. A new and distinct variety of ornamental cherry tree, substantially as herein illustrated and described.

* * * * *